US011694096B2

(12) United States Patent
Schwartz et al.

(10) Patent No.: US 11,694,096 B2
(45) Date of Patent: Jul. 4, 2023

(54) FOOT DIFFERENTIATION SCORING

(71) Applicant: Aetrex Worldwide, Inc., Teaneck, NJ (US)

(72) Inventors: Laurence I. Schwartz, New York, NY (US); Alexander Choy, Fort Lee, NJ (US)

(73) Assignee: Aetrex, Inc., Teaneck, NJ (US)

( * ) Notice: Subject to any disclaimer, the term of this patent is extended or adjusted under 35 U.S.C. 154(b) by 634 days.

(21) Appl. No.: 16/681,861

(22) Filed: Nov. 13, 2019

(65) Prior Publication Data

US 2020/0151594 A1 May 14, 2020

Related U.S. Application Data

(60) Provisional application No. 62/760,548, filed on Nov. 13, 2018.

(51) Int. Cl.
*G06N 5/04* (2023.01)
*G06N 20/00* (2019.01)
*A43D 1/02* (2006.01)
*A61F 5/01* (2006.01)
*A61B 5/103* (2006.01)
*A61B 5/107* (2006.01)
*A61B 5/00* (2006.01)

(52) U.S. Cl.
CPC ............ *G06N 5/04* (2013.01); *A43D 1/025* (2013.01); *A61B 5/0064* (2013.01); *A61B 5/1036* (2013.01); *A61B 5/1074* (2013.01); *A61B 5/1079* (2013.01); *A61F 5/0127* (2013.01); *G06N 20/00* (2019.01)

(58) Field of Classification Search
CPC .......... G06N 5/04; G06N 20/00; G06N 5/025; G06N 20/10; A43D 1/025; A43D 3/021; A61B 5/0064; A61B 5/1036; A61B 5/1074; A61B 5/1079; A61B 5/7267; A61F 5/0127; A43B 3/34; A43B 7/14; A43B 7/1415; A43B 7/18; B33Y 50/00; B33Y 80/00
USPC .............................................. 709/12; 706/12
See application file for complete search history.

(56) References Cited

U.S. PATENT DOCUMENTS

| 7,493,230 | B2 * | 2/2009 | Schwartz | ............... A43B 17/00 |
| | | | | 702/155 |
| 10,083,401 | B2 | 9/2018 | Gross et al. | |
| 11,317,824 | B1 * | 5/2022 | Uehara | ................... A61B 5/742 |
| 2011/0196264 | A1 * | 8/2011 | Asada | ................... A61B 5/4023 |
| | | | | 600/595 |
| 2014/0066816 | A1 * | 3/2014 | McNames | ............ A61B 5/6831 |
| | | | | 600/595 |

(Continued)

*Primary Examiner* — Omar Casillashernandez
(74) *Attorney, Agent, or Firm* — Lowenstein Sandler LLP

(57) ABSTRACT

Methods, systems, and non-transitory computer readable medium for foot differentiation scoring pertaining to an individual's differences in their two feet. A method includes receiving, from sensors of a scanning device, pressure and/or other measurement data corresponding to feet of a user. The method further includes preprocessing the pressure and/or measurement data. The method further includes generating, based on the preprocessed pressure and/or measurement data, a foot differentiation score based on differences between a left foot and a right foot of the user. The foot differentiation score may assign or correspond to a numerical rating based on how different the user's left foot and right foot are from each other.

23 Claims, 7 Drawing Sheets

(56) References Cited

U.S. PATENT DOCUMENTS

| | | | | |
|---|---|---|---|---|
| 2017/0281008 A1* | 10/2017 | Schwartz | ............... | G06T 7/155 |
| 2018/0199674 A1* | 7/2018 | Walker | ................... | A43B 3/36 |
| 2019/0150793 A1* | 5/2019 | Barth | .................... | A61B 5/112 |
| 2019/0313913 A1* | 10/2019 | Fu | ......................... | G16H 40/67 |
| 2020/0008745 A1* | 1/2020 | Burch, V | ............... | G16H 50/30 |

\* cited by examiner

FOOT DIFFERENTIATION SCORING

CROSS-REFERENCE TO RELATED APPLICATION(S)

This application claims the benefit of priority of U.S. Provisional Patent Application No. 62/760,548, filed on Nov. 13, 2018, the disclosure of which is hereby incorporated by reference herein in its entirety.

TECHNICAL FIELD

The present disclosure relates to differentiation scoring between an individual's two feet.

BACKGROUND

Foot problems and the corresponding costs associated with foot care cost millions of dollars each year. Foot pain and other foot-related problems often impact an individual's physical activities at work and in leisure time. Foot problems can arise from, among other things, improperly fitting footwear, improper foot alignment, poor arch support, prolonged and uncomfortable standing, walking or athletic activities, medical conditions, and the like.

Pedorthics is the art concerned with the design, manufacture, fit, and/or modification of footwear and foot appliances, including orthotics/insoles, to help prevent or alleviate foot problems caused by, among other things, overuse, injury, and medical conditions. For those who practice any level of pedorthics, the goal is to provide protection, fit, and comfort to the consumer/patient. One of the primary ways of achieving this has been to reduce foot pressure at the greatest areas of impact through the use of foot orthotics (e.g., insoles, orthotic insoles, arch supports, etc.) which are inserted into footwear to help cushion, align and support the foot as well as redistribute pressure and promote overall foot and postural wellbeing.

A human being's two feet are not identical, and individuals often have differences and variations between their two feet (e.g., size, arch depth/type, pressure, etc.). There are many different types and sizes of foot orthotics. Consequently, selecting or manufacturing the correct type and size of orthotic for a user may be challenging, especially for individuals that have certain levels of foot differentiation. Use of a standard prefabricated orthotic or an incorrect type or size of orthotic may not provide adequate protection and comfort and may promote or aggravate foot pain or other foot problems.

BRIEF DESCRIPTION OF THE DRAWINGS

The present disclosure is illustrated by way of example, and not by way of limitation in the figures of the accompanying drawings.

DETAILED DESCRIPTION

Figure 1:
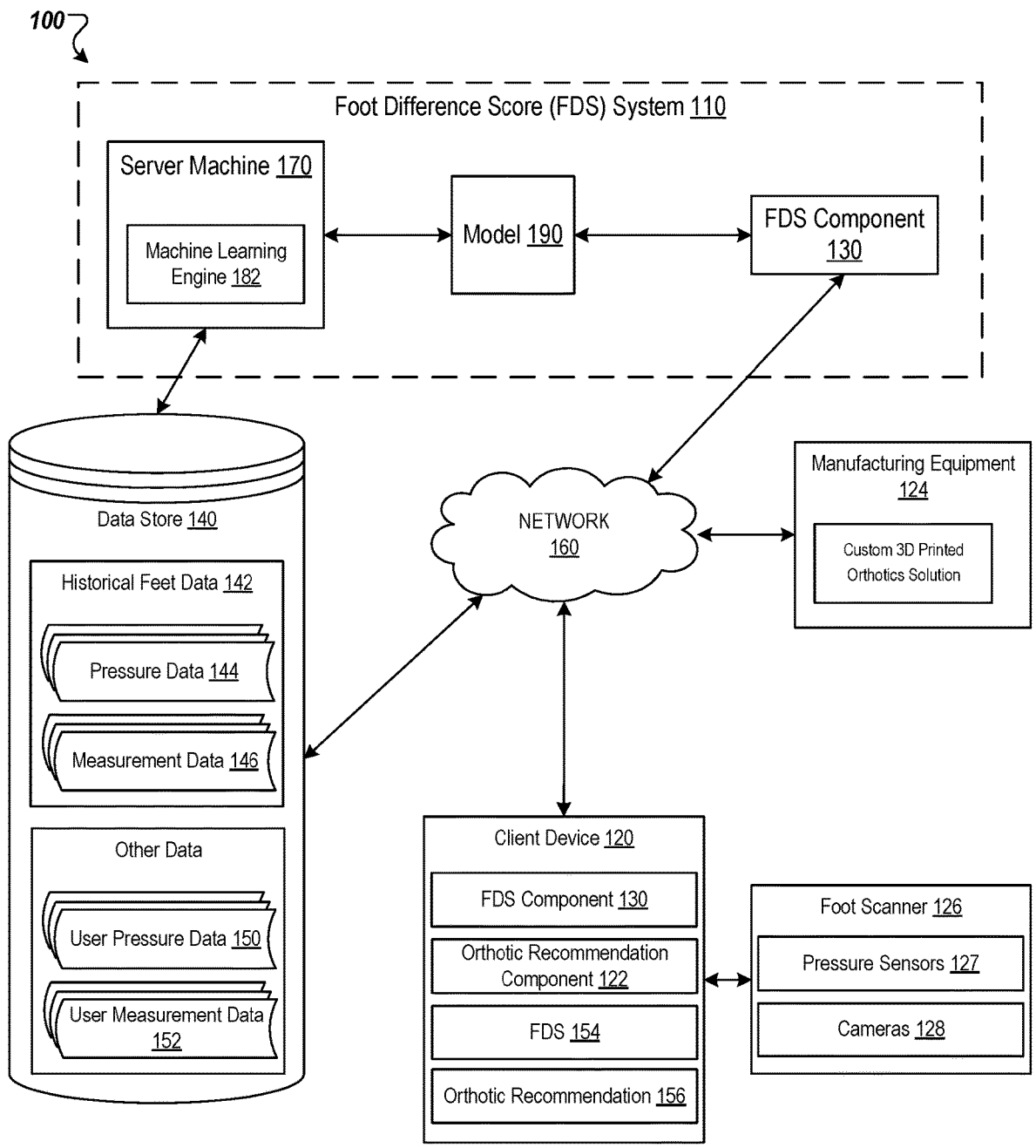
FIG. 1 is a block diagram illustrating an exemplary system architecture, according to certain embodiments.

Described herein are technologies directed to foot differentiation scoring. Foot problems (e.g., plantar fasciitis) may be painful and debilitating. Foot orthotics, such as insoles, arch supports, etc., may be used for, among other things, comfort, support, and alignment, to help alleviate certain conditions of the foot that cause pain and/or discomfort. Prefabricated orthotics may be selected or custom orthotics may be produced. However, the incorrect selection of orthotics may not provide adequate comfort or support or otherwise help alleviate foot problems in situations where individuals have meaningful foot differentiation between there left and right feet.

The devices, systems, and methods disclosed herein provide foot differentiation scoring. More specifically, the concept of foot differentiation scoring may provide an objective metric as to the extent of difference between an individual's feet. The present disclosure addresses the problem of foot differentiation and describes a method and system of measuring an individual's foot differences, assigning a foot differentiation score, advising an individual of how different the individual's feet are from each other, and utilizing same to help recommend the appropriate prefabricated or custom foot orthotic.

Pressure and measurement data corresponding to feet of a user may be received. The pressure and measurement data may be preprocessed. A foot differentiation score may be generated based on the preprocessed pressure and measurement data.

An orthotic product recommendation, whether prefabricated or custom produced, may be provided to the user based on the foot differentiation score (hereinafter, the "FDS"). The FDS may assign (e.g., to a data record associated with the user) or correspond to a numerical rating based on how different the user's left foot and right foot are from each other. The generating of the FDS may be by inputting the preprocessed pressure data and measurement data into a trained machine learning model and receiving the FDS score from the machine learning model. The machine learning model may be trained, tuned, and selected using historical feet data including, but not limited to, historical pressure and measurement data.

This machine learning model determines the degree of differences between an individual's two feet one to the other. Utilizing core machine learning principles, a data-driven metric determines foot differentiation, and in turn, the FDS.

The FDS is the percentile in which an individual is included relative to the global foot-scanned population (i.e., if an individual's FDS is 40, 40% of all foot-scanned people in the historical data bank would have feet less different than each other). The FDS is then utilized on a case-by-case basis to determine the need for a prefabricated or custom made orthotic. This FDS is one of the factors to determine whether a prefabricated or custom orthotic is recommended (e.g., a high FDS number would be indicative of a custom orthotic need because of a high degree of difference between the individual's right and left foot).

In some embodiments, the present disclosure may be to work in conjunction with the applicant's Albert® 3D foot scanner to provide an orthotic recommendation (e.g., custom 3D printed orthotics). The custom 3D printed orthotics is a personalize product based on pressure data scanned from the Albert® system. The FDS and the custom 3D printed orthotics are two synergistic products that offer a consumer the information of how different the feet are and a viable solution if the difference between the feet is too high of a tolerance.

A system and method may be provided for identifying physical properties of feet, as disclosed in U.S. patent application Ser. No. 15/475,101 filed on Mar. 30, 2017, published as U.S. Patent Publication No. 2017/0281008, the entire contents of which are hereby incorporated by reference herein.

Aspects of the present disclosure result in technological advantages of significant reduction in energy consumption (e.g., battery consumption), bandwidth, latency, and so forth. In some embodiments, the technological advantages may result from generating of a foot difference score to provide an orthotic recommendation. Generating the FDS to provide the orthotic recommendation, as disclosed herein, reduces energy consumption, required bandwidth, and latency associated with providing an incorrect orthotic recommendation, receiving feedback that the orthotic recommendation was incorrect, and generating a new orthotic recommendation until a correct orthotic recommendation is provided. Aspects of the present disclosure also result in technological advantages of providing a correct orthotic recommendation for a particular user. Incorrect orthotic recommendations may be produced for a user, transported to a user, and used by a user. Providing a correct orthotic recommendation reduces material waste, transportation waste, etc. of incorrectly produced and/or used orthotics.

FIG. 1 is a block diagram illustrating an exemplary system architecture 100, according to certain embodiments. The system architecture 100 includes client device 120, manufacturing equipment 124, scanning device 126, a foot differentiation score (FDS) component 130 (e.g., server or application programming interface (API)), and a data store 140. The FDS component 130 may be part of an FDS system 110. The FDS system 110 may further include server machine 170.

The client device 120, manufacturing equipment 124, scanning device 126, FDS component 130, data store 140, and server machine 170 may be coupled to each other via a network 160 for generating an FDS 154.

The FDS 154, which indicates the globally foot-scanned percentile that the individual falls within, is then utilized in the orthotic recommendation process to determine whether a prefabricated or custom 3D printed orthotic is recommended for that individual's needs. The FDS 154 is based on differentiations of all or many of the features captured by the foot scanning device between the feet of the individual being scanned. For example, the differentiations may be in arch depth between the left foot and the right foot. In another example, differentiations may be in pressure distribution between the left foot and the right foot. In another example, differentiations may be in arch depth between the left foot and the right foot. In another example, differentiations may be in arch type designations (e.g., flat, low, med, or high arch).

In some embodiments, network 160 is a public network that provides client device 120 with access to the FDS component 130, data store 140, and other publicly available computing devices. In some embodiments, network 160 is a private network that provides client device 120 with access to the FDS component 130, data store 140, and other privately available computing devices. Network 160 may include one or more wide area networks (WANs), local area networks (LANs), wired networks (e.g., Ethernet network), wireless networks (e.g., an 802.11 network or a Wi-Fi network), cellular networks (e.g., a Long Term Evolution (LTE) network), routers, hubs, switches, server computers, and/or a combination thereof.

The client device 120 may include a computing device such as personal computers (PCs), laptops, mobile phones, smart phones, tablet computers, netbook computers, network connected televisions ("smart TV"), network-connected media players (e.g., Blu-ray player), a set-top-box, over-the-top (OTT) streaming devices, operator boxes, etc. The client device 120 may include an orthotic recommendation component 122. Orthotic recommendation component 122 may receive user input (e.g., via a graphical user interface (GUI) displayed via the client device 120) and may cause the scanning device 126 to generate pressure data 150 and measurement data 152 corresponding to the feet of the user. The orthotic recommendation component 122 may receive the pressure data 150 and measurement data 152 from the scanning device 126 and may transmit the pressure data 150 and measurement data 152 to the FDS component 130. The orthotic recommendation component 122 may receive an FDS 154 from the FDS component 130 based on the pressure data 150 and measurement data 152. Orthotic recommendation component 122 may cause an orthotic recommendation 156 to be provided to the user based on the FDS 154. In some embodiments, the orthotic recommendation component 122 may cause the FDS 154 to be displayed via a GUI of the client device 120. In some embodiments, the orthotic recommendation component 122 causes a visual representation of an orthotic product to be displayed via a GUI of the client device 120 based on the FDS 154. In some embodiments, the orthotic recommendation component 122 causes an orthotic product to be provided to be provided to the user based on the FDS 154.

In some embodiments, the orthotic recommendation component 122 may cause a GUI to be displayed via the client device 120 to receive user input of user information (e.g., name, address, gender, etc.) and to receive a user request to provide the orthotic product to the user. The orthotic recommendation component 122 may transmit information (e.g., the FDS 154, orthotic recommendation 156, user information, user request for orthotic product, etc.) to the manufacturing equipment 124 to cause the manufacturing equipment 124 to generate (e.g., manufacture) the orthotic product for the user based on the FDS 154.

In some embodiments, one or more functionalities of the orthotic recommendation component may be performed by the FDS component 130 or the scanning device 126. In some embodiments, the scanning device 126 and the client device 120 may be integrated into a single device.

The manufacturing equipment 124 may produce the orthotic product based on information (e.g., FDS 154, orthotic recommendation 156, user input, etc.) received from the orthotic recommendation component 122 which determination and recommendation may be made by manual methods or by an automated process (e.g., machine learning). The orthotic product may include one or more of shoe insert, foot orthosis, orthotic, arch support, orthotic insole, etc. An orthotic product may provide support for the foot by redistributing pressure and/or ground reaction forces acting on the foot joints while standing, walking, or running. An orthotic product may be pre-fabricated (e.g., off-the-shelf) or custom made by 3D printing or other methods (e.g., according to the FDS 154, orthotic recommendation 156, pressure data 150 and measurement data 152, etc.). An orthotic product may accommodate biomechanical deformities and soft tissue conditions. An orthotic product may reduce pain for high-arched feet, rheumatoid arthritis, plantar fasciitis, hallux valgus, juvenile idiopathic arthritis, etc. An orthotic product may be used to prevent pain, foot ulcers, etc.

The scanning device 126 may be used to scan one or more feet. In one embodiment, one foot may be placed inside the scanning device 126 for scanning. In another embodiment, a pair of feet may be placed inside the scanning device 126 for scanning (e.g., both feet may be in the scanning device 126 during the scanning). The scanning device may include pressure sensors 127 and measurement sensors 128. The pressure sensors 127 may be part of a pressure plate (e.g., pressure mat). In some embodiments, once pressure sensor 127 may be located every square centimeter ($cm^2$) of surface area of the pressure plate. A user may stand with the feet of the user on the pressure plate and the pressure sensors 127 within the pressure plate may provide pressure measurements of the distribution of the user's weight on the feet. The measurement sensors 128 may be infrared light emitting diodes (IR LEDs) that measure different dimensions of the feet. In some embodiments, the scanning device 126 may include about 18 cameras to take images for calculation of distances. In one embodiment, the scanning device 126 is an "Albert® device" or "Albert® scanner." In some embodiments, the scanning device 126 may be as described in U.S. patent application Ser. No. 15/475,101 filed on Mar. 30, 2017, published as U.S. Patent Publication No. 2017/0281008, the entire contents of which are hereby incorporated by reference herein.

In some embodiments, a system may include the scanning device 126, a memory, and a processing device, coupled to the memory and scanning device 126. The scanning device 126 may be a foot scanning device configured for obtaining pressure data 150 and measurement data 152 corresponding to feet of a user. The memory may store the pressure data 150 and measurement data 152. The processing device may receive the pressure data 150 and measurement data 152 corresponding to the feet of the user, preprocess the pressure data 150 and the measurement data 152, generate, based on the preprocessed pressure and measurement data, a FDS 154, and cause an orthotic recommendation 156 to be provided to the user based on the FDS 154. In some embodiments, the scanning device 126 includes the memory and the processing device. In some embodiments, the client device 120 includes the memory and the processing device, and the client device 120 is coupled to the scanning device 126. In some embodiments, the client device 120 includes the processing device and the data store 140 includes the memory and the processing device is coupled to the scanning device 126 and the data store 140.

The FDS component 130 be implemented on one or more computing devices such as a rackmount server, a router computer, a server computer, a personal computer, a mainframe computer, a laptop computer, a tablet computer, a desktop computer, etc. to generate an FDS 154 and/or an orthotic recommendation 156. In some embodiments, the FDS component 130 may use pressure data 150 and measurement data 152 to generate an FDS 154. In some embodiments, the FDS component 130 may use a trained machine learning model 190 to generate an FDS 154. A machine learning model 190 may be trained using historical feet data 142 for predicting FDS 154.

The FDS component 130 may receive (e.g., receive from client device 120 or scanning device 126, retrieve from the data store 140, etc.) pressure data 150 and measurement data 152, preprocess the pressure data 150 and measurement data 152, and generate an FDS 154 based on the preprocessed pressure and measurement data. The FDS component 130 may cause an orthotic recommendation 156 to be provided to the user based on the FDS 154. In some embodiments, the FDS component 130 causes the orthotic recommendation 156 to be provided to the user by causing a GUI on the client device 120 to display the FDS 154. In some embodiments, the FDS component 130 causes the orthotic recommendation 156 to be provided to the user by causing a GUI on the client device 120 to display a visual representation of an orthotic product based on the FDS 154. In some embodiments, the FDS component 130 causes the orthotic recommendation 156 to be provided to the user by causing the orthotic product to be provided to the user based on the FDS 154 (e.g., transporting the orthotic product to the user, causing the manufacturing equipment 124 to custom manufacture the orthotic product, etc.). In some embodiments, FDS component 130 causes the orthotic recommendation 156 to be provided to the user by providing the FDS 154 to the orthotic recommendation component 122 to cause the orthotic recommendation component 122 to provide the orthotic recommendation 156 to the user. In some embodiments, FDS component 130 causes the orthotic recommendation 156 to be provided to the user without transmitting the FDS 154 to the orthotic recommendation component 122.

Data store 140 may be utilized to accumulate and store the data used to calculate the percentile portion of the FDS. The data store 140 may be a memory (e.g., random access memory), a drive (e.g., a hard drive, a flash drive), a database system, or another type of component or device capable of storing data. Data store 140 may include multiple storage components (e.g., multiple drives or multiple databases) that may span multiple computing devices (e.g., multiple server computers). The data store 140 may store one or more of historical feet data 142 including historical pressure data 144 and historical measurement data 146, pressure data 150, measurement data 152, FDS 154, or orthotic recommendations 156. The historical feet data 142 may include data collected from use of a scanning device 126 over a period of time.

In some embodiments, the client device may store pressure data 150 and measurement data 152 in the data store 140 and the FDS component 130 may retrieve the pressure data 150 and measurement data 152 from the data store. In some embodiments, the FDS component 130 may store the FDS 154 in the data store 140 and the client device 120 may retrieve the FDS 154 from the data store 140.

In some embodiments, FDS system 110 further includes server machine 170. The server machine 170 may be one or more computing devices (such as a rackmount server, a router computer, a server computer, a personal computer, a mainframe computer, a laptop computer, a tablet computer, a desktop computer, etc.), data stores (e.g., hard disks, memories databases), networks, software components, or hardware components.

Server machine 170 includes a machine learning engine 182 that uses compiled and stored data in the data store 140 to train a machine learning model. Some operations of the machine learning engine 182 are described in detail below with respect to FIG. 5. The machine learning engine 182 may partition the historical feet data 142 into a training set (e.g., ninety percent of the historical feet data). The partitioning of the historical feet data 142 may be via k-fold cross-validation.

In k-fold cross-validation, an original sample (e.g., historical feet data 142) may be randomly partitioned into k equal sized subsamples. Of the k subsamples, a single subsample is retained as the validation data for testing the model, and the remaining k−1 subsamples are used as training data. The cross-validation process is then repeated k times, with each of the k subsamples used exactly once as the validation data. The k results can then be averaged to produce a single estimation. Observations (e.g., historical feet data 142) may be used for both training and validation, and each observation is used for validation exactly once. In some embodiments, 10-fold cross-validation may be used. In some embodiments, k may be an unfixed parameter. For example, setting k=2 results in 2-fold cross-validation. In 2-fold cross-validation, the dataset is randomly shuffled into two sets d0 and d1, so that both sets are equal size (which may be implemented by shuffling the data array and then splitting it in two). Training may be on d0 and validating may be on d1, followed by training on d1 and validating on d0. In some embodiments, the folds are selected so that the mean response value is approximately equal in all the folds. In the case of binary classification, each fold may contain roughly the same proportions of the two types of class labels. In some embodiments, scores are generated based on target values, with the target values corresponding to metrics such as one or more of area, pressure distribution, max weight, arch depth, dorsal height, length, width, arch type, etc. Training data may include target scores, which may be learned based on defined rules used to predict the scores.

In some embodiments, the machine learning model 190 may use one or more of a decision tree or a support vector machine (SVM). The machine learning model 190 may be composed of a single level of linear or non-linear operations (e.g., SVM) or may be a deep network (e.g., a machine learning model that is composed of multiple levels of non-linear operations). In some embodiments, the machine learning model 190 may use an SVM gradient algorithm. The SVM gradient algorithm may be used to predict scores based on gradient boosting regression.

FDS component 130 may provide current data (e.g., pressure data 150 and measurement data 152) as input to trained machine learning model 190 and may run trained machine learning model 190 on the input to obtain one or more outputs.

In some embodiments, the pressure data 150 and measurement data 152 includes features. The features may include one or more of area, pressure distribution, max weight, arch depth, dorsal height, length, width, arch type, etc. In certain embodiments that utilize labels, the FDS component 130 may label the pressure data 150 and measurement data 152. For example, a label may include custom orthotics for one or more of a distribution greater than 7 percent, custom orthotics for an arch depth greater than 0.5 cm, or custom orthotics for a differentiation in arch type greater than 2 levels. In other embodiments that utilize a score-based approach, rules may be defined to help predict scores. For example, a score may be computed as follows: each point of pressure differentiation contributes two points to the score; every 1 mm of arch depth distance contributes one point to the score; every point of arch depth sensor differentiation (e.g., every 5 mm of arch depth) contributes 15 points.

For purpose of illustration only, rather than limitation, aspects of the disclosure describe the training of a machine learning model and use of a trained learning model using information pertaining to pressure data 150 and measurement data 152 to generate FDS 154 to provide an orthotic recommendation 156 to a user. In other implementations, a heuristic model or rule-based model is used to determine an FDS 154. FDS component may monitor historical feet data 142. Any of the information described with respect to data inputs may be monitored or otherwise used in the heuristic or rule-based model.

In some embodiments, the functions of client device 120, FDS component 130, and server machine 170 may be provided by a fewer number of devices. For example, in some embodiments server machine 170 and FDS component 130 may be integrated into a single device. In some embodiments, the functionality of the FDS component 130 is performed exclusively by the client device 120, by the FDS system 110, some other device, or some of the functionality may be split across one or more devices of the system architecture 100. In general, functions described in one embodiment as being performed by client device 120, FDS component 130, and server machine 170 can also be performed on FDS component 130 in other embodiments, if appropriate. In addition, the functionality attributed to a particular component can be performed by different or multiple components operating together. For example, in some embodiments, the FDS component 130 may generate the orthotic recommendation 156 based on the FDS 154. In another example, client device 120 may preprocess the pressure data 150 and measurement data 152 (e.g., generate the additional data such as distribution, levels of arch type, etc.) to be input into the trained machine learning model.

In addition, the functions of a particular component can be performed by different or multiple components operating together. One or more of the FDS component 130, or server machine 170 may be accessed as a service provided to other systems or devices through appropriate application programming interfaces (API).

Although embodiments of the disclosure are discussed in terms of scanning devices, feet differentiation scores, and orthotic recommendations for feet of a user, embodiments may also be generally applied to differentiation scores and optimizing recommendations.

Figure 2:
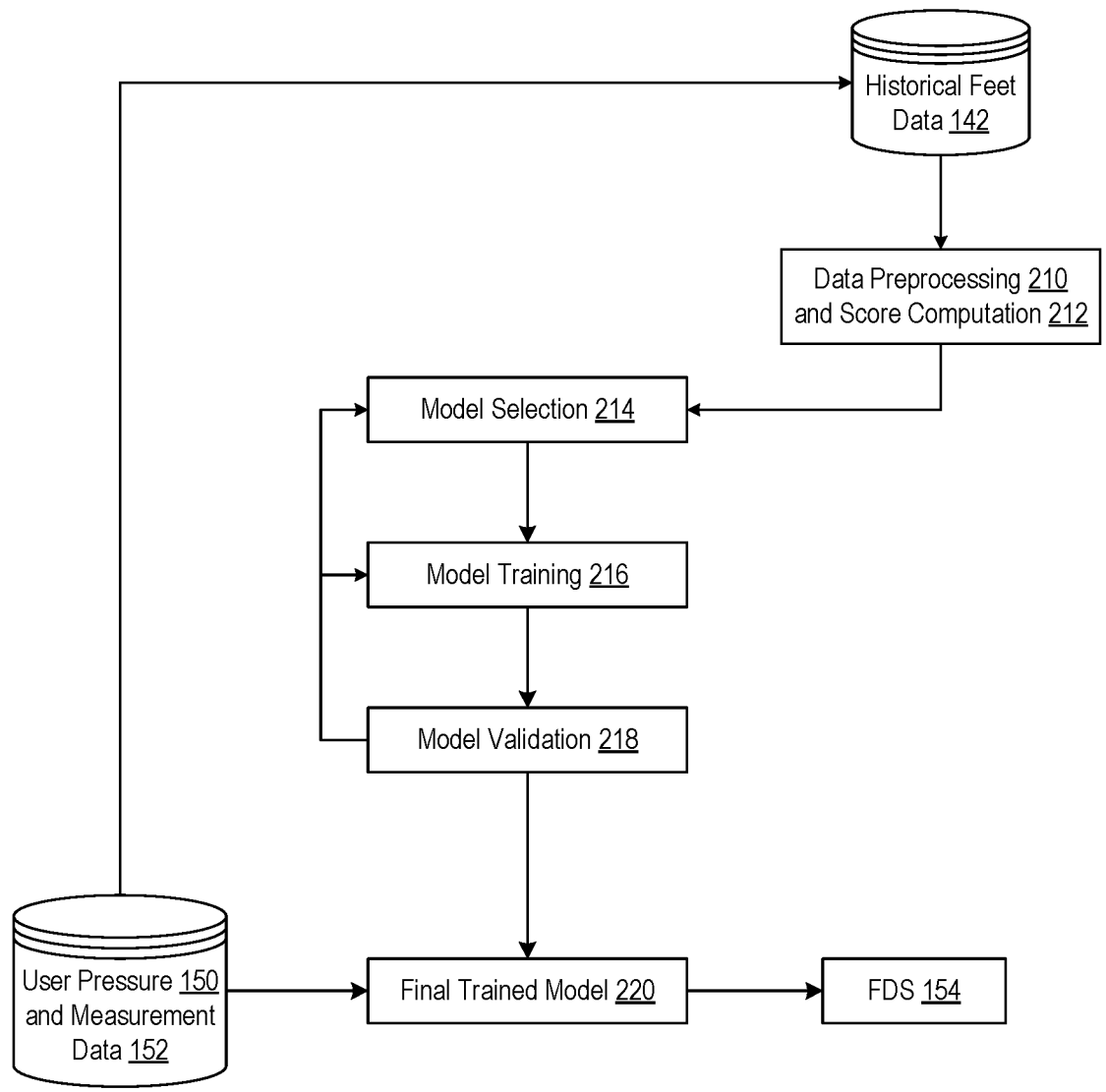
FIG. 2 is a block diagram illustrating generating a predicted foot differentiation score, according to certain embodiments.

FIG. 2 is a block diagram illustrating a system 200 for calculating an FDS 154, according to certain embodiments. The system 200 may be a feedback system for predicting FDS 154 based on pressure data 150 and measurement data 152.

At block 210, the system 200 (e.g., FDS system 110 of FIG. 1) performs data preprocessing (e.g., via machine learning engine 182 of server machine 170 of FIG. 1) of the historical feet data 142 to load rules for generating scores. In some embodiments, the system 200 generates a plurality of sets of features corresponding to each of the data sets.

At block 212, the system 200 performs score computation to generate scores for the preprocessed data based on the loaded rules. For example, a score generated for a pair of feet may be computed based on one or more identified differences between the two feet (e.g., a difference in arch depth).

At block 214, the system 200 performs model selection. For example, different models (e.g., algorithms) may be tested. In some embodiments, the selected model includes a support vector machine (SVM) algorithm.

At block 216, the system 200 performs model training for score prediction, and at block 218 the system performs model validation. In some embodiments, a first percentage (e.g., 90%) of the historical feet data 142 is used to train the model and a second percentage (e.g., the remaining 10%) of the historical feet data 142 that was not used for the training is used to validate the model. Model validation may be used to determine whether the model is over-fit to the first percentage of the historical feet data. After training the model with the first percentage and validating the model with the second percentage, the model may be trained with the full amount (e.g., 100%) of the historical feet data 142).

At block 220, the final trained model is used. Pressure data 150 and measurement data 152 of a user may be input into the final trained model. An FDS 154 may be output from the trained model.

The pressure data 150, measurement data 152, and FDS 154 may be used at block 212 (e.g., via a feedback loop) where the pressure data 150 and measurement data 152 are used to update (e.g., re-train) the trained model via model training.

FIGS. 3-6 are flow diagrams illustrating example methods 300-600 associated with generating FDS 154 to cause an orthotic recommendation 156 to be provided to a user, according to certain embodiments. Methods 300-600 be performed by processing logic that may include hardware (e.g., circuitry, dedicated logic, programmable logic, microcode, processing device, etc.), software (such as instructions run on a processing device, a general purpose computer system, or a dedicated machine), firmware, microcode, or a combination thereof. In one embodiment, methods 300-600 may be performed, in part, by FDS system 110. In some embodiments, methods 300-600 may be performed by FDS component 130. In some embodiments, a non-transitory computer-readable storage medium stores instructions that when executed by a processing device (e.g., of FDS system 110) cause the processing device to perform methods 300-600.

For simplicity of explanation, methods 300-600 are depicted and described as a series of acts. However, acts in accordance with this disclosure can occur in various orders and/or concurrently and with other acts not presented and described herein. Furthermore, not all illustrated acts may be performed to implement the methods 300-600 in accordance with the disclosed subject matter. In addition, those skilled in the art will understand and appreciate that the methods 300-600 could alternatively be represented as a series of interrelated states via a state diagram or events.

Figure 3:
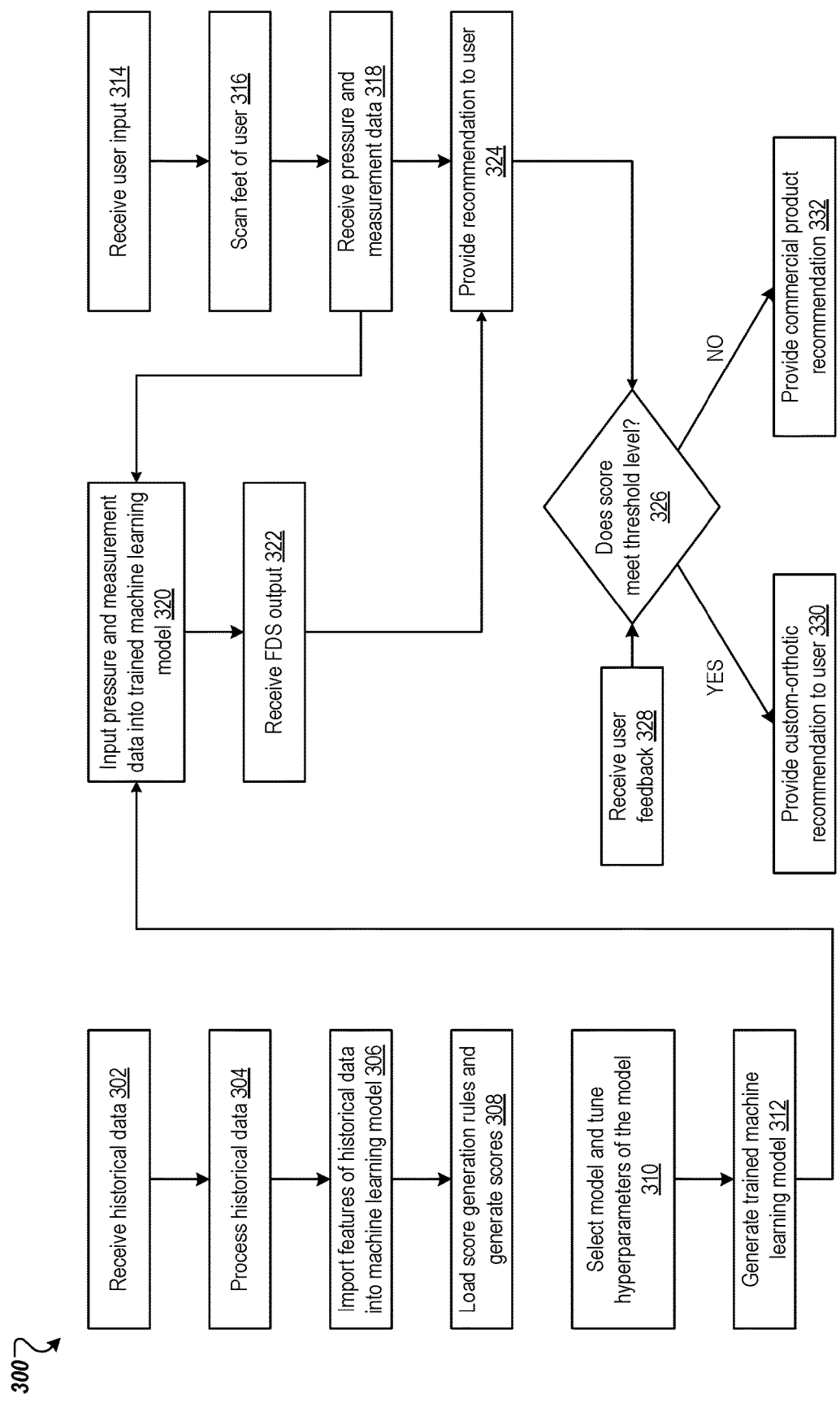
FIG. 3 is a flow diagram illustrating an example method of generating a foot differentiation score, according to certain embodiments.

FIG. 3 is a flow diagram of a method 300 that may cause an orthotic recommendation 156 to be provided to a user based on FDS 154, according to certain embodiments. Method 300 may be performed by one or more components of system architecture 100 (e.g., the FDS system 110 and the client device 120).

At block 302, processing logic (e.g., of FDS system 110, data set generator 172, FDS component 130, etc.) receives historical feet data 142 (e.g., data in an Albert® Scan Database, historical feet data 142 including pressure data 150 and measurement data 152 from an Albert® scanning device) stored in a data store 140 (e.g., a data store of Amazon Web Services, compiled in a data store).

At block 304, processing logic (e.g., of FDS system 110) processes the historical feet data 142. The historical feet data 142 may be exported from the data store 140 via MySQL. At block 304, the processing of the historical feet data 142 may include converting categorical data to be represented in numerical values. At block 304, the processing of the historical feet data 142 may include normalizing the historical feet data 142 by subtracting the mean and dividing by the standard deviation.

At block 306, processing logic (e.g., of FDS system 110) may feed features of the historical feet data 142 into the machine learning model 190. The features may include one or more of area, pressure distribution, max weight, arch depth, dorsal height, length, width, arch type, etc.

At block 308, processing logic (e.g., of FDS system 110) may load score generation rules (e.g., from the data store 140) and generate scores based on the historical data for training the machine learning model. The processing logic may use empirical rules to generate scores. In some embodiments, the empirical rules include custom orthotics for pressure distribution greater than 7 percent. In some embodiments, the empirical rules include custom orthotics for arch depth greater than 0.5 cm. In some embodiments, the empirical rules include custom orthotics for an arch type greater or equal to two levels (e.g., at least two level differentiation between feet). In some embodiments, the empirical rules include the following rules for computing a score: each point of pressure differentiation contributes two points to the score; every 1 mm of arch depth distance contributes one point to the score; every 5 mm of arch depth differentiation contributes 15 points.

At block 310, processing logic (e.g., of FDS system 110) selects a model and tunes the hyperparameters of the model 190 in order to perform score prediction. For example, after generating different machine learning models (e.g., testing various algorithms), a model is selected as the machine learning model 190 (e.g., based on being more accurate than the other machine learning models). In some embodiments, the machine learning model 190 may use a Support Vector Machine (SVM) algorithm. At block 310, the tuning of the hyperparameters may be performed to select settings for the model 190 (e.g., to select settings for the SVM algorithm).

At block 310, the machine learning model 190 may be evaluated by looking at the model accuracy and receiver operating characteristic area under curve (ROC-AUC) using 10-fold cross validation (e.g., 90% of the historical feet data 142 is used to train and 10% of the historical feet data 142 is used to validate). In some embodiments, selected hyperparameters for the machine learning model 190 may include C=571 (e.g., a value for how well the model 190 works for new data) and gamma=0.004 (e.g., training accuracy). In some embodiments, the metrics of the machine learning model 190 may be an accuracy of 94.1+/1 0.86% and AUC of 98.13+/−0.53%.

At block 312, processing logic (e.g., of FDS system 110) generates a trained machine learning model 190 using the historical feet data 142 and tuned parameters. The trained machine learning model 190 may be hosted by FDS component 130 (e.g., Aetrex web server or API) for receiving pressure data 150 and measurement data 152 and outputting FDS (see blocks 320-322).

At block 314, a processing logic (e.g., of client device 120) may receive user input from a user. The user input may include user information (e.g., identifying information, shoe information, activity level information, age, gender, etc.). The user input may include a request to perform a scan of the feet of the user.

At block 316, the processing logic (e.g., of client device 120) causes the scanning device 126 to scan the feet of the user to generate pressure data 150 using the pressure sensors 127 and to generate measurement data 152 using the measurement sensors or cameras 128.

At block 318, the processing logic (e.g., of client device 120) receives the pressure data 150 and measurement data 152 from the scanning device 126.

At block 320, the processing logic (e.g., of the client device 120) causes the pressure data 150 and measurement data 152 to be input into the trained machine learning model 190. For example, the processing logic (e.g., of the client device 120) may transmit the pressure data 150 and measurement data 152 to FDS system 110 (e.g., FDS component 130). The FDS component 130 may input the pressure data 150 and measurement data 152 into the trained machine learning model 190.

At block 322, the processing logic (e.g., of client device 120) may receive FDS 154 output from the trained machine learning model 190 responsive to the input of pressure data 150 and measurement data 152.

At block 324, the processing logic (e.g., of client device 120) causes an orthotic recommendation to be provided to the user based on the FDS 154. In some embodiments, at block 324, the processing logic causes a GUI to display the FDS 154. In some embodiments, at block 324, the processing logic causes a GUI to display a visual representation of an orthotic product based on the FDS 154. In some embodiments, at block 324, the processing logic causes the orthotic product to be provided to the user based on the FDS 154.

At block 326, the processing logic (e.g., of client device 120) determines whether differentiations between the feet of the user meet a threshold level of differentiations (e.g., whether computed score exceeds a threshold score). In some embodiments, the processing logic determines whether the FDS 154 indicates that the differentiations between the feet of the user meet a threshold level of differentiations (e.g., to recommend custom orthotics).

At block 328, the processing logic (e.g., of client device 120) may receive user feedback (e.g., from a store technician, from a customer) corresponding to the FDS 154. The user feedback may be used by the processing logic in block 326 to determine whether the differentiations between the feet of the user meet a threshold level of differentiations.

At block 330, in response to determining the differentiations between the feet of the user meet a threshold level of differentiations, the processing logic (e.g., of client device 120) causes an orthotic recommendation 156 of 3D-printed custom orthotics to be provided to the user based on the FDS 154.

At block 332, in response to determining the differentiations between the feet of the user do not meet a threshold level of differentiations, the processing logic (e.g., of client device 120) causes an orthotic recommendation 156 of commercial orthotics to be provided to the user based on the FDS 154.

In some embodiments, at block 330 and 332, the processing logic causes a GUI to display the orthotic recommendation 156 based on the FDS 154. In some embodiments, at block 330 and 332, the processing logic causes a GUI to display a visual representation of an orthotic product based on the orthotic recommendation 156. In some embodiments, at block 330 and 332, the processing logic causes the orthotic product to be provided (e.g., transported, manufactured and delivered, etc.) to the user based on the FDS 154.

Figure 4:
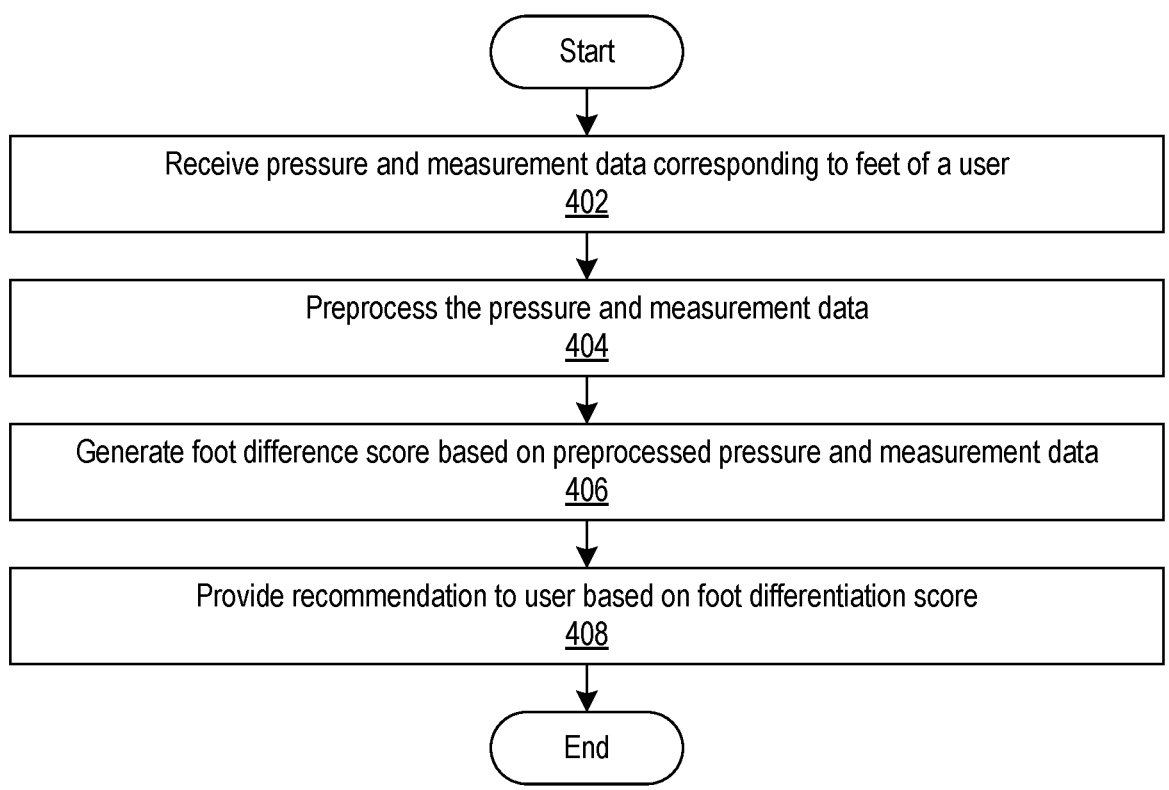
FIG. 4 is a further flow diagram illustrating an example method of generating a foot differentiation score, according to certain embodiments.

FIG. 4 is a flow diagram of a method 400 for generating FDS 154 to cause an orthotic recommendation 156 to be provided to a user, according to certain embodiments.

Referring to FIG. 4, at block 402 the processing logic receives pressure data 150 and measurement data 152 corresponding to feet of a user. In some embodiments, the pressure data 150 is from pressure sensors 127 of a scanning device 126 and the measurement data 152 is from measurement sensors 128 or cameras of the scanning device.

At block 404, the processing logic preprocesses the pressure data 150 and the measurement data 152. Preprocessing may include normalizing the pressure data 150 and the measurement data 152.

At block 406, the processing logic generates, based on the preprocessed pressure and measurement data, FDS 154. In some embodiments, the FDS 154 may be based on a percentile (e.g., FDS 154) that the user corresponding to the pressure data 150 and measurement data 152 would benefit from use of custom orthotics (e.g., would have a greater reduction of pain using custom orthotics than using off-the-shelf orthotics). The percentile that the user would benefit from use custom orthotics may be higher based on differentiations between the feet of the user (e.g., different arch type, different arch depth, and different pressure distribution).

At block 408, the processing logic causes an orthotic recommendation 156 to be provided to the user based on the FDS 154. For example, the processing logic may inform the user of FDS 154 and/or may offer orthotics solutions based on the FDS 154.

Figure 5:
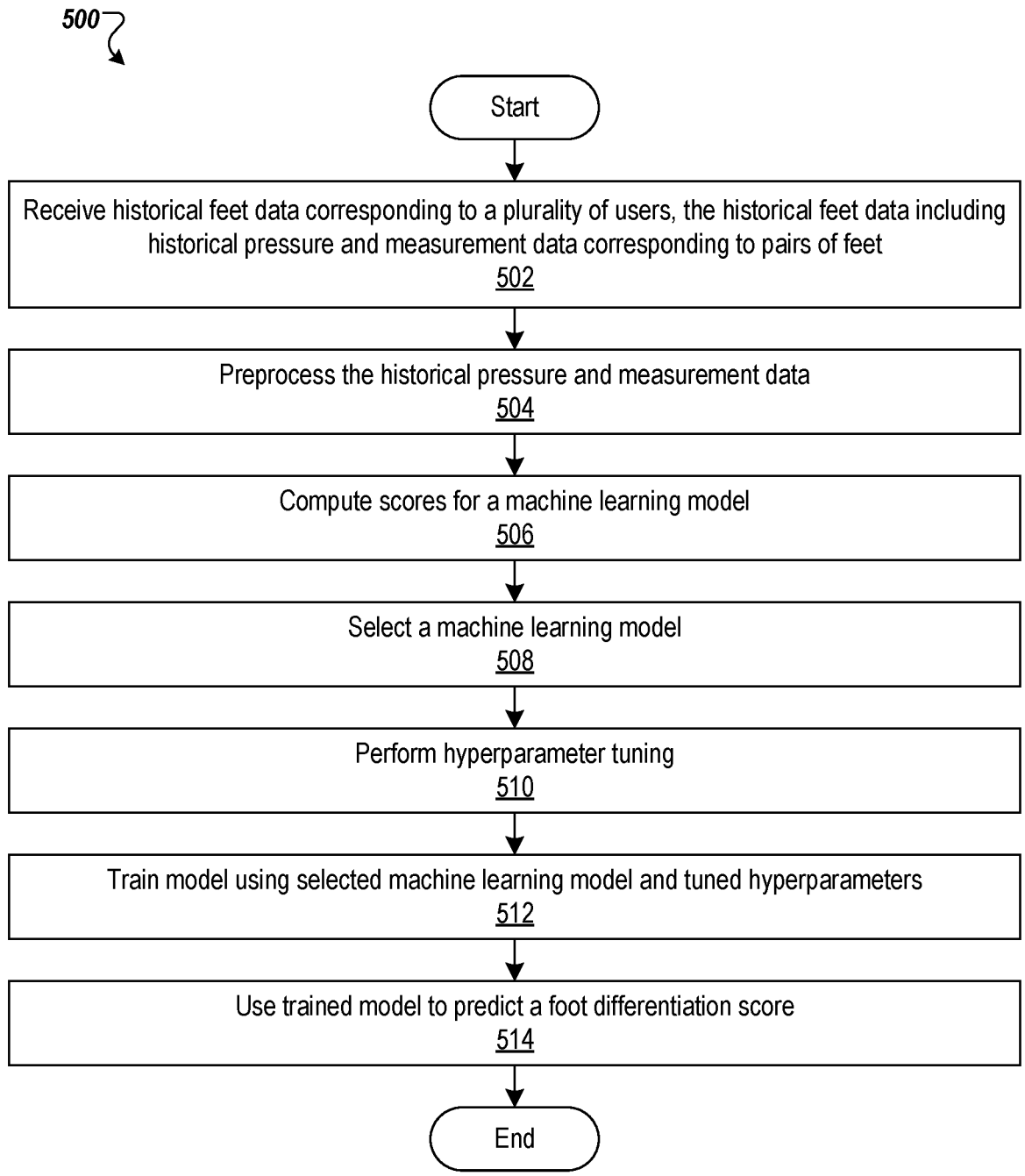
FIG. 5 is a further flow diagram illustrating an example method of generating a foot differentiation score, according to certain embodiments.

FIG. 5 is a flow diagram of a method 500 for using a machine learning model to generate FDS 154 for providing an orthotic recommendation 156 to the user, according to certain embodiments.

At block 502, the processing logic receives historical feet data 142 corresponding to a plurality of users. The historical feet data 142 may include historical pressure data 144 and historical measurement data 146 corresponding to pairs of feet. In some embodiments, data from scans via the scanning device 126 (e.g., data from Albert® scans) may be saved to a database of a relational database service (RDS) hosted by a data store 140 (e.g., Amazon Web Services (AWS)). The processing logic may use MySQL to query the requested features and the data may be exported into a text file (e.g., a comma-separated values (.csv) file). For example, the data queried may correspond to features including one or more of LeftTotalArea, RightTotalArea, LeftTopArea, RightTopArea, LeftBottomArea, RightBottomArea, LeftTotalDist, RightTotalDist, LeftTopDist, RightTopDist, LeftBottomDist, RightBottomDist, LeftMaxWeightTop, RightMaxWeightTop, LeftMaxWeightBottom, RightMaxWeightBottom, LeftArchHeightMm, RightArchHeightMm, LeftDorsalHeightMm, RightDorsalHeightMm, LeftLengthMm, RightLengthMm, LeftWidthMm, RightWidthMm, LeftArch, or RightArch (references to "dorsal" height is used interchangeably with "instep" height).

At block 504, the processing logic preprocesses the historical pressure data 144 and historical measurement data 146. The processing logic may remove duplicate scans (e.g., via a pandas module) from the data. The processing logic may convert gender entries from strings to 0 and 1. The processing logic may clean up a feature called LeftArch and RightArch. There may be four types of arch (e.g., flat, low, med, and high) that the processing logic may convert into discrete numbers (e.g., 0, 1, 2, and 3 respectively). Since flat is close to low, numbering these features in this way may be appropriate since they are close together in physical type.

At block 506, the processing logic computes scores for a machine learning model (e.g., using one or more of arch depth, arch type, pressure distribution, etc.). In some embodiments, the processing logic may receive input of labels for corresponding portions of the historical feet data 142 (e.g., manual input for labeling the results by hand). In some embodiments, the processing logic may automatically label historical feet data 142 without manual input. In some embodiments, the processing logic may use an algorithm that takes the differentiation of key points and take extremes of that data as a label (e.g., about 20% of the data may be 1's).

In some embodiments, the processing logic may receive rules for computing scores based on differences in physical characteristics between pairs of feet. In some embodiments, responsive to the processing logic determining that the differentiation of the pressure distribution on the top (e.g., forefoot) of the respective feet was greater than 7% (e.g., greater than 7% differentiation in pressure placed on forefoot of left foot and forefoot of right foot), the processing logic may determine that the custom orthotics are to be used. In some embodiments, responsive to the processing logic determining that the differentiation of the arch types is at least two levels (e.g., flat vs. medium, low vs. high, etc.), the processing logic may determine that custom orthotics are to be used. In some embodiments, responsive to the processing logic determining that the differentiation in arch depth is 0.5 cm or greater, the processing logic may determine that custom orthotics are to be used. Using these empirical rules, it may be determined that 19.902% users from the historical feet data 142 are to use custom orthotics.

Since the historical feet data 142 is multivariate and the values can span a large range, the preprocessing may include normalizing the values of the historical feet data 142 by feature (e.g., via a function in scikit-learn called sklearn-.preprocessing.StandardScaler( ).) Normalizing the historical feet data 142 may include subtracting data by the mean and dividing by the standard deviation.

At block 508, the processing logic selects a machine learning model (e.g., machine learning algorithm) by trying comprehensive list and picking a machine learning model with the best accuracy. In some embodiments, the machine learning model is a Support Vector Machine (SVM) which may include a prime algorithm to be used with the historical feet data 142. SVM may be used with a smaller amount of data (e.g., 9,000 data points or less from the database for Albert® scans).

At block 510, the processing logic performs hyperparameter tuning using exhaustive grid search and 10-fold cross validation to tune model parameters. In some embodiments, the SVM may include parameters that may be tuned to account for conditions such as class imbalance and overfitting. SVM may create a multidimensional hyperplane in the space of the features inputted that would be used to classify data (e.g., classify as corresponding to a particular FDS 154). The SVM may map data from the feature space to another defined hyperplane, thus allowing more complex datasets to be discriminated properly. Use of kernel functions (e.g., radial basis function (RBF) kernel) by SVM may allow computationally efficient learning in the hyperplane space.

At block 512, the processing logic trains a final model using selected machine learning algorithm and tuned hyperparameters. The processing logic may train and validate the model using 10-fold cross validation, looking at accuracy and ROC-AUC. 10-fold cross validation may be implemented to assess, from multiple iterations, how the model would perform. Other metrics may be calculated, such as sensitivity and specificity. The metric of AUC may be used to determine how well the model can classify based on differing threshold. The AUC is the area under the curve of a receiver operator characteristic curve. Since the model is to output a percentile score a high AUC may indicate that the output of the model meets a threshold percentile for a given input.

The processing logic may use a tool (e.g., from Scikit-Learn called GridSearchCV) that iterates through a plurality of hyperparameters (e.g., set up by the user) and finds the optimal parameter (e.g., that corresponds to the most accurate model of a plurality of models that use different parameters) for training the machine learning model. In some embodiments, the processing logic may select the parameters c=571 and gamma=0.04. After using these parameters, a trained model may have an accuracy of 94.1+/−0.86% and an AUC of 98.13+/−0.53%.

At block 514, the processing logic deploys the trained machine learning model for predicting a FDS 154, which is subsequently used for providing an orthotic recommendation 156 to the user. After determining an optimal algorithm settings and hyperparameters (e.g., that corresponds to the most accurate model of a plurality of models using at least one of different algorithm settings or hyperparameters), the processing logic trains the final model and deploys the trained final model in a API environment (other embodiments may include server environment or client hosted environment) to be called on by other clients (e.g., Albert® personal computers (PCs), client devices 120) responsive to a request to generate an FDS 154. The model may compute the FDS 154 in about 20 milliseconds (ms).

Figure 6:
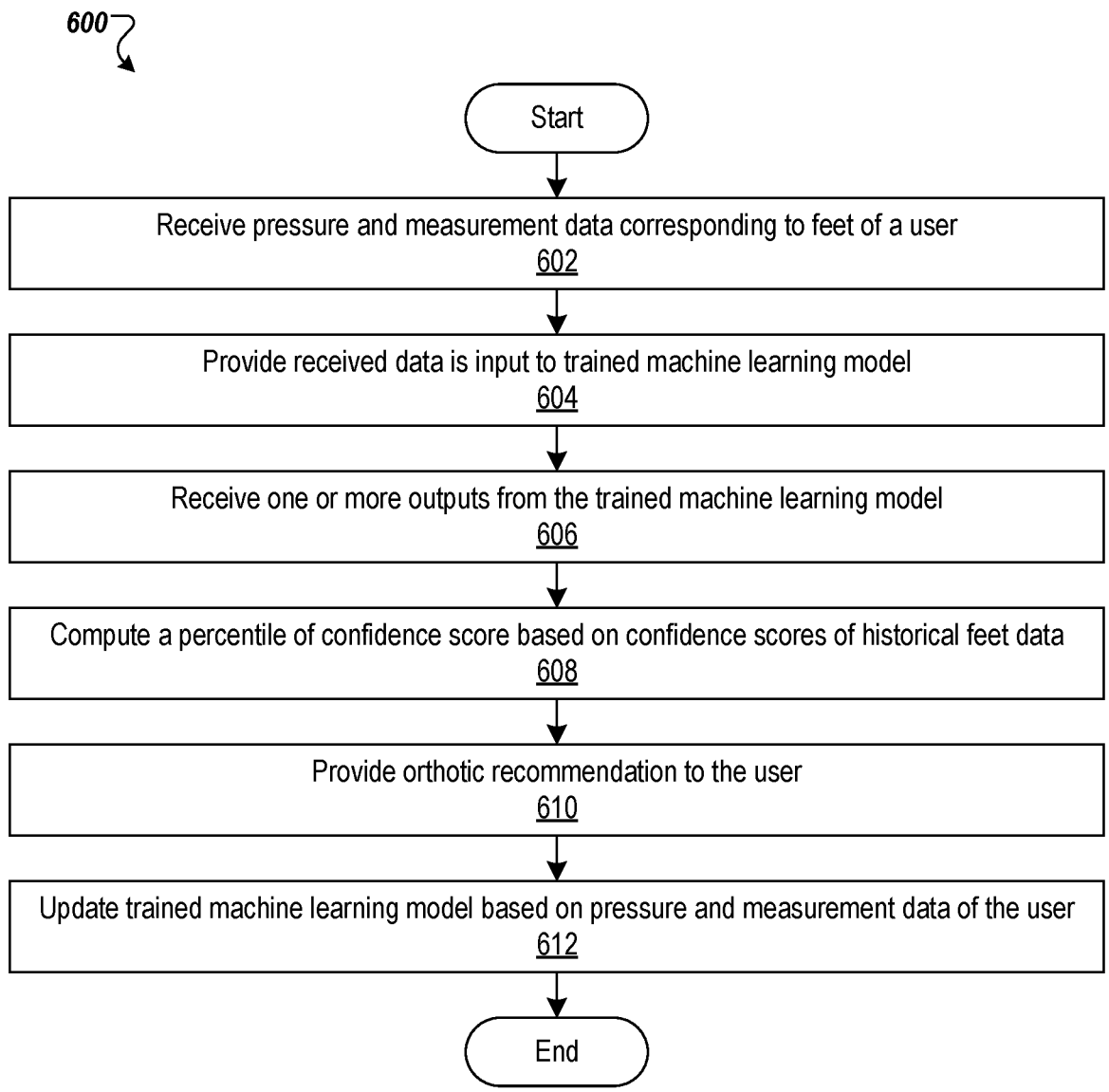
FIG. 6 is a further flow diagram illustrating an example method of generating a foot differentiation score, according to certain embodiments.

FIG. 6 is a flow diagram of a method 600 for updating the trained machine learning model for determining FDS 154 to provide an orthotic recommendation 156, according to certain embodiments.

At block 602 the processing logic receives pressure data 150 and measurement data 152 (e.g., data corresponding to Albert® foot scans) corresponding to feet of a user.

At block 604 the processing logic provides the pressure data 150 and the measurement data 152 as input to a trained machine learning model.

At block 606 the processing logic obtains one or more outputs from the trained machine learning model. In some embodiments, the one or more outputs include a predicted FDS 154. In some embodiments, the one or more outputs include a confidence score of foot differentiation from inputted data.

At block 608, the processing logic computes a percentile of confidence score based on confidence scores of all historical feet data 142 (e.g., the processing logic extracts, from the one or more outputs, a percentile of a FDS 154).

At block 610 the processing logic causes, based on the FDS 154 and the level of confidence, an orthotic recommendation 156 to be provided to the user. For example, the processing logic may output the FDS 154 to the user.

At block 612 the processing logic updates the trained machine learning model based on the pressure data 150 and measurement data 152 of the user (e.g., via a feedback loop).

Figure 7:
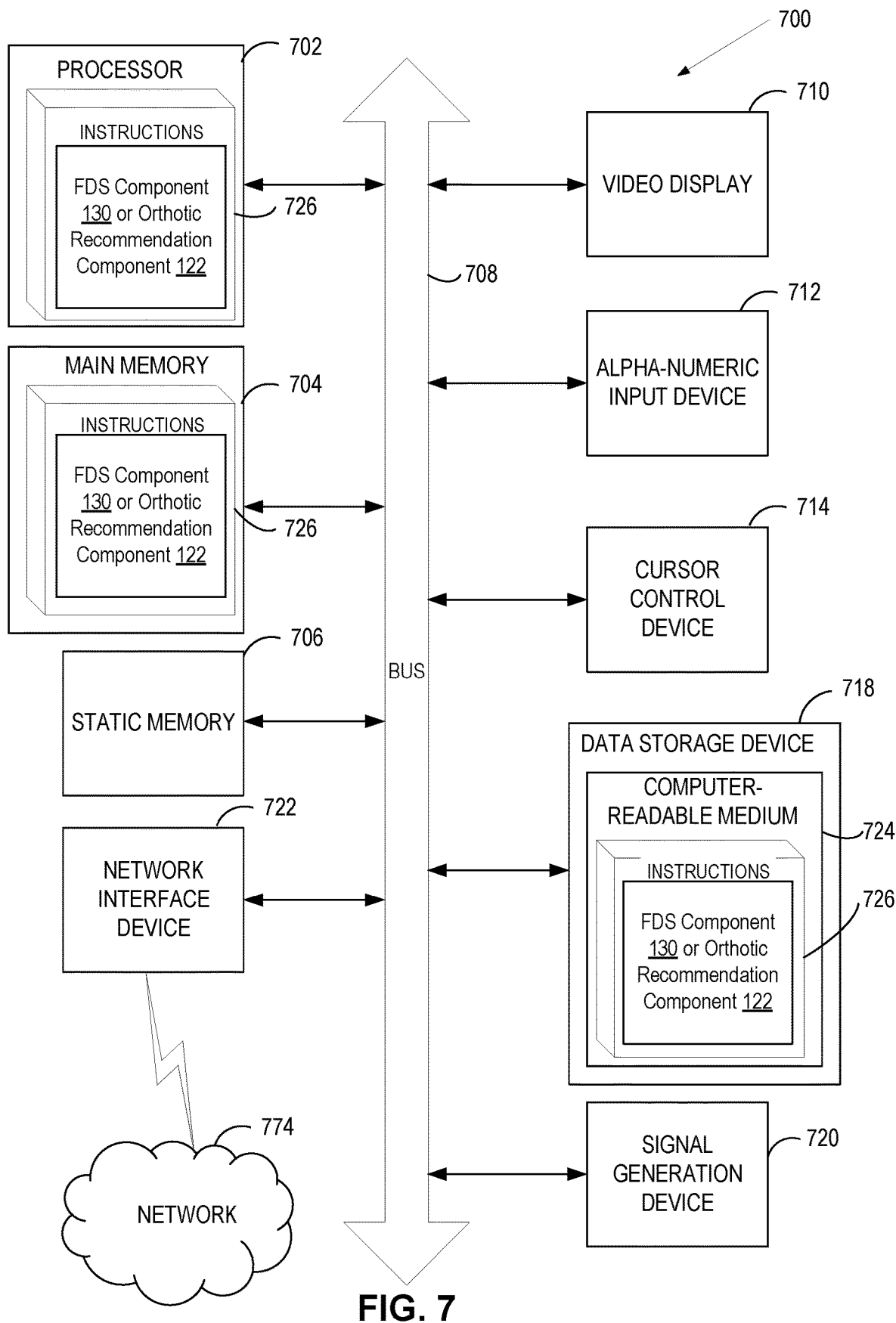
FIG. 7 is a block diagram illustrating a computer system, according to certain embodiments.

FIG. 7 is a block diagram illustrating a computer system 700, according to certain embodiments. In some embodiments, computer system 700 may be connected (e.g., via a network, such as a Local Area Network (LAN), an intranet, an extranet, or the Internet) to other computer systems. Computer system 700 may operate in the capacity of a server or a client computer in a client-server environment, or as a peer computer in a peer-to-peer or distributed network environment. Computer system 700 may be provided by a personal computer (PC), a tablet PC, a set-top box (STB), a Personal Digital Assistant (PDA), a cellular telephone, a web appliance, a server, a network router, switch or bridge, or any device capable of executing a set of instructions (sequential or otherwise) that specify actions to be taken by that device. Further, the term "computer" shall include any collection of computers that individually or jointly execute a set (or multiple sets) of instructions to perform any one or more of the methods described herein.

In a further aspect, the computer system 700 may include a processing device 702, a volatile memory 704 (e.g., random access memory (RAM)), a non-volatile memory 706 (e.g., read-only memory (ROM) or electrically-erasable programmable ROM (EEPROM)), and a data storage device 716, which may communicate with each other via a bus 708.

Processing device 702 may be provided by one or more processors such as a general purpose processor (such as, for example, a complex instruction set computing (CISC) microprocessor, a reduced instruction set computing (RISC) microprocessor, a very long instruction word (VLIW) microprocessor, a microprocessor implementing other types of instruction sets, or a microprocessor implementing a combination of types of instruction sets) or a specialized processor (such as, for example, an application specific integrated circuit (ASIC), a field programmable gate array (FPGA), a digital signal processor (DSP), or a network processor).

Computer system 700 may further include a network interface device 722. Computer system 700 also may include a video display unit 710 (e.g., an LCD), an alpha-numeric input device 712 (e.g., a keyboard), a cursor control device 714 (e.g., a mouse), and a signal generation device 720.

In some implementations, data storage device 716 may include a non-transitory computer-readable storage medium 724 on which may store instructions 726 encoding any one or more of the methods or functions described herein, including instructions encoding the FDS component 130 or orthotic recommendation component 122 of FIG. 1 and for implementing methods described herein.

Instructions 726 may also reside, completely or partially, within volatile memory 704 and/or within processing device 702 during execution thereof by computer system 700, hence, volatile memory 704 and processing device 702 may also constitute machine-readable storage media.

While non-transitory computer-readable storage medium 724 is shown in the illustrative examples as a single medium, the term "computer-readable storage medium" shall include a single medium or multiple media (e.g., a centralized or distributed database, and/or associated caches and servers) that store the one or more sets of executable instructions. The term "computer-readable storage medium" shall also include any tangible medium that is capable of storing or encoding a set of instructions for execution by a computer that cause the computer to perform any one or more of the methods described herein. The term "computer-readable storage medium" shall include, but not be limited to, solid-state memories, optical media, and magnetic media.

The methods, components, and features described herein may be implemented by discrete hardware components or may be integrated in the functionality of other hardware components such as ASICS, FPGAs, DSPs or similar devices. In addition, the methods, components, and features may be implemented by firmware modules or functional circuitry within hardware devices. Further, the methods, components, and features may be implemented in any combination of hardware devices and computer program components, or in computer programs.

Unless specifically stated otherwise, terms such as "receiving," "preprocessing," "generating," "causing," "inputting," "receiving," "partitioning," "training," "selecting," "validating," "providing," "performing," "predicting," "changing," "testing," "obtaining," "extracting," "determining," "updating," or the like, refer to actions and processes performed or implemented by computer systems that manipulates and transforms data represented as physical (electronic) quantities within the computer system registers and memories into other data similarly represented as physical quantities within the computer system memories or registers or other such information storage, transmission or display devices. Also, the terms "first," "second," "third," "fourth," etc. as used herein are meant as labels to distinguish among different elements and may not have an ordinal meaning according to their numerical designation.

Examples described herein also relate to an apparatus for performing the methods described herein. This apparatus may be specially constructed for performing the methods described herein, or it may include a general purpose computer system selectively programmed by a computer program stored in the computer system. Such a computer program may be stored in a computer-readable tangible storage medium.

The methods and illustrative examples described herein are not inherently related to any particular computer or other apparatus. Various general purpose systems may be used in accordance with the teachings described herein, or it may prove convenient to construct more specialized apparatus to perform methods described herein and/or each of their individual functions, routines, subroutines, or operations. Examples of the structure for a variety of these systems are set forth in the description above.

The above description is intended to be illustrative, and not restrictive. Although the present disclosure has been described with references to specific illustrative examples and implementations, it will be recognized that the present disclosure is not limited to the examples and implementations described. The scope of the disclosure should be determined with reference to the following claims, along with the full scope of equivalents to which the claims are entitled.

What is claimed is:

1. A method comprising:
   receiving, from sensors of a scanning device configured to perform pressure measurements and/or capture foot images, pressure and/or measurement data corresponding to feet of a user;
   preprocessing the pressure and/or measurement data; and
   generating, based on the preprocessed pressure and/or measurement data, a foot differentiation score that assigns a numerical rating based on how different the user's left foot and right foot are from each other, wherein the foot differentiation score is generated based at least in part on rules that assign points to the foot differentiation score based on threshold conditions met by the preprocessed pressure and/or measurement data.

2. The method of claim 1, further comprising:
   causing an orthotic recommendation to be provided to the user based on the foot differentiation score.

3. The method of claim 1, wherein the generating of the foot differentiation score comprises:
   inputting the preprocessed pressure and/or measurement data into a trained machine learning model; and
   receiving, from the trained machine learning model, the foot differentiation score.

4. The method of claim 3, wherein the trained machine learning model is trained based on historical pressure and/or measurement data compiled in a data bank, wherein the method further comprises storing the pressure and/or measurement data in the data bank for further training of the trained machine learning model.

5. The method of claim 1, wherein generating the foot differentiation score comprises:
  partitioning preprocessed historical pressure and/or measurement data into a training set and a validation set; and
  training a machine learning model for foot differentiation scoring to cause orthotic recommendations to be provided to users, wherein the training of the machine learning model comprises tuning hyperparameters of the learning model based on rule-based scoring.

6. The method of claim 5, wherein generating the foot differentiation score further comprises:
  validating the trained machine learning model using the validation set.

7. The method of claim 6, wherein partitioning the preprocessed historical pressure and/or measurement data into the training set and the validation set comprise using k-fold cross-validation.

8. The method of claim 2, wherein providing the orthotic recommendation comprises one or more of:
  causing a graphical user interface (GUI) to display the foot differentiation score to inform the user of the differences between the left foot and the right foot of the user;
  causing the GUI to display a visual representation of an orthotic product based on the foot differentiation score; or
  causing the orthotic product to be provided to the user based on the foot differentiation score through available prefabricated orthotics or custom orthotics provided by 3D printing or other method.

9. A system comprising:
  a foot scanning device configured for obtaining pressure and/or image data corresponding to feet of a user;
  a memory to store the pressure and/or image data; and
  a processing device, coupled to the memory and the foot scanning device, wherein the processing device is to:
    receive, from sensors of the foot scanning device, pressure and/or measurement data corresponding to feet of a user;
    preprocess the pressure data and/or measurement data derived from the image data; and
    generate, based on the preprocessed pressure and/or measurement data, a foot differentiation score that assigns a numerical rating based on how different the user's left foot and right foot are from each other, wherein the foot differentiation score is generated based at least in part on rules that assign points to the foot differentiation score based on threshold conditions met by the preprocessed pressure and/or measurement data.

10. The system of claim 9, wherein to generate the foot differentiation score, the processing device is to further:
  cause an orthotic recommendation to be provided to the user based on the foot differentiation score.

11. The system of claim 9, wherein to generate the foot differentiation score, the processing device is to further:
  input the preprocessed pressure and/or measurement data into a trained machine learning model; and
  receive, from the trained machine learning model, the foot differentiation score.

12. The system of claim 11, wherein the trained machine learning model is trained based on historical pressure and/or measurement data compiled in a data bank, wherein the processing device is to further store the pressure and/or measurement data in the data bank for further training of the trained machine learning model.

13. The system of claim 9, wherein to generate the foot differentiation score, the processing device is to further:
  partition preprocessed historical pressure and/or measurement data into a training set and a validation set; and
  train a machine learning model for foot differentiation scoring to cause orthotic recommendations to be provided to users, wherein the training of the machine learning model comprises tuning hyperparameters of the learning model based on rule-based scoring.

14. The system of claim 13, wherein to generate the foot differentiation score, the processing device is to further:
  validate the trained machine learning model using the validation set.

15. The system of claim 14, wherein the processing device is to use k-fold cross-validation to partition the preprocessed historical pressure and/or measurement data into the training set and the validation set.

16. The system of claim 10, wherein to provide the orthotic recommendation, the system is to:
  cause a graphical user interface (GUI) to display the foot differentiation score to inform the user of the differences between the left foot and the right foot of the user;
  cause the GUI to display a visual representation of an orthotic product based on the foot differentiation score; or
  cause the orthotic product to be provided to the user based on the foot differentiation score through available prefabricated orthotics or custom orthotics provided by 3D printing or other method.

17. A non-transitory computer-readable storage medium having instructions encoded thereon that, when executed by a processing device, cause the processing device to:
  receive, from sensors of a foot scanning device configured to perform pressure measurements and/or capture images of feet, pressure and/or measurement data corresponding to feet of a user;
  preprocess the pressure and/or measurement data; and
  generate, based on the preprocessed pressure and/or measurement data, a foot differentiation score that assigns a numerical rating based on how different the user's left foot and right foot are from each other, wherein the foot differentiation score is generated based at least in part on rules that assign points to the foot differentiation score based on threshold conditions met by the preprocessed pressure and/or measurement data.

18. The non-transitory computer-readable storage medium of claim 17, wherein the instructions further cause the processing device to:
  cause an orthotic recommendation to be provided to the user based on the foot differentiation score.

19. The non-transitory computer-readable storage medium of claim 17, wherein to generate the foot differentiation score, the instructions further cause the processing device to:
  input the preprocessed pressure and/or measurement data into a trained machine learning model; and
  receive, from the trained machine learning model, the foot differentiation score.

20. The non-transitory computer-readable storage medium of claim 19, wherein the trained machine learning model is trained based on historical pressure and/or measurement data compiled in a data bank, wherein the instructions further cause the processing device to store the pressure and/or measurement data in the data bank for further training of the trained machine learning model.

21. The non-transitory computer-readable storage medium of claim 17, wherein to generate the foot differentiation score, the instructions further cause the processing device to:
partition preprocessed historical pressure and/or measurement data into a training set and a validation set;
train a machine learning model for foot differentiation scoring to cause orthotic recommendations to be provided to users, wherein the training of the machine learning model comprises tuning hyperparameters of the learning model based on rule-based scoring; and
validate the trained machine learning model using the validation set.

22. The non-transitory computer-readable storage medium of claim 21, wherein the instructions further cause the processing device to use k-fold cross-validation to partition the preprocessed historical pressure and/or measurement data into the training set and the validation set.

23. The non-transitory computer-readable storage medium of claim 18, wherein to provide the orthotic recommendation, the instructions further cause the processing device to:
cause a graphical user interface (GUI) to display the foot differentiation score to inform the user of the differences between the left foot and the right foot of the user;
cause the GUI to display a visual representation of an orthotic product based on the foot differentiation score; or
cause the orthotic product to be provided to the user based on the foot differentiation score through available prefabricated orthotics or custom orthotics provided by 3D printing or other method.

* * * * *